United States Patent [19]

Garito

[11] 4,439,514

[45] Mar. 27, 1984

[54] PHOTORESISTIVE COMPOSITIONS

[75] Inventor: Anthony F. Garito, Radnor, Pa.

[73] Assignee: University Patents, Inc., Norwalk, Conn.

[21] Appl. No.: 340,471

[22] Filed: Jan. 18, 1982

Related U.S. Application Data

[63] Continuation of Ser. No. 113,552, Jan. 21, 1980, abandoned, which is a continuation-in-part of Ser. No. 52,007, Jun. 25, 1979, abandoned.

[51] Int. Cl.$^3$ .................................................. G03C 1/68
[52] U.S. Cl. ..................................... 430/272; 430/270; 430/495; 430/496; 430/935
[58] Field of Search ............... 430/270, 272, 495, 496, 430/935

[56] References Cited

U.S. PATENT DOCUMENTS

| | | | |
|---|---|---|---|
| 3,811,895 | 5/1974 | Ehrlich | 430/495 |
| 3,822,134 | 7/1974 | Rasch et al. | 430/539 |
| 3,911,169 | 10/1975 | Lesaicherre | 427/96 |
| 4,168,982 | 9/1979 | Pazos | 430/281 |

OTHER PUBLICATIONS

Tieke, et al: The Quantum Yield of the Topochemical Photopolymerization of Diacetylenes in Multilayers, Makromol. Chem. 179, 1639–1642 (1978).
Lieser, et al.: Polymerization of Diacetylenes in Multilayers, Journal of Polymer Science, vol. 17, 1631–1644 (1979).
Kalyanaraman, et al.: Synthesis of Nitrophenoxymethyl Substituted Diacetylene Monomers, Makromol. Chem. vol. 180, May (1979) 1393–1398.
Plueddemann: "Mechanism of Adhesion Through Silane Coupling Agents" in Composite Materials, Brautman, Krock eds. vol. 6, Ch. 6, Academy Press (1974).

*Primary Examiner*—Won H. Louie, Jr.
*Attorney, Agent, or Firm*—Woodcock, Washburn, Kurtz, Mackiewicz & Norris

[57] ABSTRACT

Photographic and Photolithographic systems are provided which utilize diacetylenic materials as components thereof. Such materials, which include at least two acetylenic bonds in conjugation with one another, provide a combination of both high sensitivity and high resolving power, thus resulting in superior photographic and photolithographic properties.

In accordance with a preferred embodiment of the invention, a substrate is coated with at least one layer of a polymerizable composition comprising a diacetylenic species, said layer being organized into a plurality of domains having a substantially regular array of the diacetylenic species. In other embodiments, covalent bonding of the diacetylenic layer to the substrate is accomplished through the use of suitably constituted silane species, thus to provide a highly beneficial adhesion of substrate and photo- or photolithographic layer.

16 Claims, 3 Drawing Figures

PHOTORESISTIVE COMPOSITIONS

This work has been supported by funds from the Defense Advance Research Projects Agency, project designation DAAK 70-77C0045.

RELATED APPLICATION

This is a continuation of application Ser. No. 113,552, filed Jan. 21, 1980, abandoned, which is a continuation-in-part of Ser. No. 052,007 filed June 25, 1979, abandoned.

BACKGROUND OF THE INVENTION

This invention is concerned with novel coating compositions, with processes for their application and use, and with articles which are formed thereby. More particularly, the invention is drawn to coatings which are useful in the art of photography and photolithography and especially to a new genus of coatings for photo-resistive, photographic and other purposes which employ diacetylenes. According to a preferred embodiment, such coatings may be formulated which comprise a plurality of domains, which domains exhibit a uniquely regular structure; such embodiment yields photographic films and photolithographic materials of exceedingly high resolution and efficiency.

The diacetylenic compositions taught hereby offer vastly improved properties for photography and photo-lithography as compared with the materials known to the prior art. Thus, greatly improved efficiency, impermeability, structural regularity, resolution, contrast, and adhesion to substrates are evidenced. A direct comparison with commonly employed photoresistive materials may be had. While known materials such as glycidyl methacrylate, polybutene sulfone and polymethyl methacrylate have quantum efficiencies on the order of 0.1 or less, the diacetylenic species taught by the present invention have quantum efficiencies from $10^8$ to $10^{12}$ molecules reacted per photon. Similarly, while the prior art materials require a radiation absorption of from 10–20 to 300–500 joules per cubic centimeter to achieve the cited quantum efficiencies, the diacetylenes of the present invention require only about 0.03 joules per cubic centimeter. Additionally, while currently used photo-resists have resolving powers of about 10,000 Å, and 2000–3000 Å in extreme cases, the resists of the present invention may resolve structure as small as 100 Å. Thus, it will be readily appreciated by those skilled in the art that the diacetylenic coating compositions taught by the present invention represent a very substantial advance in the photographic and photolithographic arts.

Photo-lithography finds its roots in 1852 when British Patent No. 565 was issued to Talbot for a bichromate sensitized gelatin coating which was useful for differential etching of copper by ferric chloride. Since this time, numerous compositions and processes have been developed which serve to transfer a pattern of light or other radiant energy onto a substrate through the intermediation of a coating sensitive to such radiant energy. The art of photolithography has developed broadly in recent decades to include various modes of printing, etching, and image reproduction from macro to micro scales, and has fostered the development of entire new industries. See generally, *Photo-Resist Materials and Processes* by William DeForest, McGraw-Hill 1975.

One industry which has placed heavy reliance upon the use of photolighography is that of microstructure fabrication. This industry which produces structures imposed upon surfaces of thin films having extremely small dimensions is the basis for the production of information processing, electronics, switching, and other devices which rely upon "integrated" electronics, the fabrication and interconnection of large numbers of very small device structures on a single piece of silicon or other substrate.

Exemplary uses of photolithography employing what is commonly denominated in the art as photo-resists, are described in *Science*, volume 196, No. 4293, pp 945–949, May 27, 1977, by R. W. Keyes. As taught in the Keyes article, a substrate, usually silicon, is caused to be coated with a layer of electrically non-conductive material, frequently silicon dioxide, usually by "growth" from the substrate itself through a suitable oxidizing process. The substrate is then further coated with one or more layers of photo-resist. At this time, selected portions of the photo-resist are exposed to a suitable form of radiant energy, which irradiation causes an alteration of the structure or physical characteristics of the portions of the resist thus exposed. Thus, electromagnetic energy such as light, especially ultraviolet light; x-radiation, laser radiation, etc. and particle radiation such as electron beam, particle beam, and plasma radiation may be utilized to alter the structure or physical characteristics of the portion of the photo-resist irradiated.

Following the irradiation of the selected portions of the photo-resist and concomitant alteration of the structure or physical characteristics thereof, a distinction may be drawn between the selected portions of the resist and those not selected based upon the altered structure or physical characteristics. Thus, the selected portions may be viewed as being either more or less suited to removal from the underlying substrate than are the unselected portions through any appropriate means. The selected portions may be either more or less soluble in a liquid medium, may have a higher or lower vapor pressure, may exhibit greater or lesser resistance to chemical attack, or may evidence any other differing structure or characteristic which may facilitate differential removal from the substrate as compared to the unselected portions. Based upon one or more of these distinctions, the selected (irradiated) portions of the photo-resist are either removed from the substrate while the unselected (unexposed) portions remain, or the selected portions are retained while the unselected portions are removed. By analogy with traditional photographic processes, the former process is carried out with photo-resists denominated as "positive" resists while the latter employ "negative" photo-resists.

The selection of certain portions of a photo-resist for irradiation may be accomplished in various ways, all of which are well known to those skilled in the art. Masking is a common procedure which is performed by placing over the surface of a photo-resist-coated substrate (or composite substrate) a mask, usually formed photographically, and by causing the passage of radiation through the mask onto the resist layer. The mask is designed so as to have transmissive and non-transmissive areas corresponding to the portions of the resist layer which have been chosen for irradiation and for non-irradiation respectively. As is well known to those skilled in the art, the radiant energy used in conjunction with the masking technique may benefit from being collimated, focused, monochromatized, or rendered coherent. Such persons will also recognize that all portions of the electromagnetic spectrum may be employed with the masking technique as may various forms of particle irradiation such as electron beams, ion beams, and plasma irradiation.

It is also well known to irradiate selected portions of a resist layer without the use of masking. Thus direct projection of a radiant energy beam, especially a laser, electron, or particle beam may be undertaken to irradiate the selected portions of the layer. Such projection is usually controlled by automated means and often by a computer. It is to be understood that the means and mechanisms for irradiating selected portions of the photoresist layer are well known in the art. See, for example, proceedings of the IEEE, volume 62, No. 10, pp 1361–1387, October, 1974, Henry I. Smith, *Fabrication Techniques for Surface-Acoustic-Wave and Thin-Film Optical Devices; X-Ray Optics: Applications to Solids* (Ed. H. J. Queisser); E. Spiller and R. Feder, *X-ray Lithography*, pp 35–92 Springer (1977); and *Ann. Rev. Mat. Sci.*, vol. 6, pp 267–301, L. F. Thompson and R. E. Kerwin, *Polymer Resist Systems for Photo-and Electron Lithography.*

It may be seen that following the irradiation of the selected portions of the photo-resist and the selected removal either of the selected portions of those portions not selected, a pattern will remain on the substrated formed of irradiated or non-irradiated photo-resist depending upon whether a negative or positive resist formulation was employed. This photo-resist pattern will alternate with exposed substrate, usually silicon oxide. The exposed silicon oxide (or other) substrate) layer segments or portions are then subject to treatment. In nearly all cases, the oxide layer is removed or etched away in manners well known to those skilled in the art. The etching away of the silicon oxide layer is designed to expose the underlying silicon substrate to treatment and processing. The etching of the silicon oxide layer is intended to be accomplished only in the areas not covered with portions of photo-resist. The photo-resist must therefore be relatively insensitive to the etching means employed to remove the exposed oxide portions.

After the etching off of the oxide layer the remaining photo-resist is removed to yield a pattern of exposed silicon and silicon oxide or other substrate formulation. The exposed silicon is then treated to alter its electrical characteristics, frequently through processes denominated as "doping". "Doping", which is well known to those skilled in the art, causes elements such as phosphorous or boron to be diffused into the exposed silicon or other substrate material. The treatment of the article after the removal of the photo-resist is not directly related to this embodiment of the invention and is well know to those skilled in the art. The treated article may subsequently be re-coated with photo-resistive materials, exposed selectively, and caused to undergo differential removal of resist, etching, and treatment one or more additional times to result in complex surface structures on the substrate. A selectively exposed and removed resist layer may also be used for the deposition of metal or other conductive materials onto the surface of the substrate to serve as electrical contacts with the variously treated surface areas as is well known to those skilled in the art.

It is to be understood that the foregoing background is not intended as a rigorous delineation of the metes and bounds of the microfabrication art and that numerous variations, both of materials and processes are known. It should be further understood that the term "photo-resist" has been adopted by those skilled in the art as a generic term descriptive of all forms of radiation-sensitive coatings useful in lithography. Thus, the term embraces coatings useful for microfabrication, etching, printing, and compositing as well as numerous others. Similarly, the term "photo-resist" has been adopted for those coatings which are sensitive to particulate radiation such as electron beams.

It is apparent from the foregoing that the characteristics of the photo-resists useful in a particular photolithographic process is of central importance to the success of that process. In general, it is recognized by those skilled in the art that the ideal photo-resist will exhibit certain exemplary qualities. Thus, a photo-resist should be capable of ultra-fine resolution, and should exhibit a high response to incident radiation. Additionally, an exemplary photo-resist should be easily applied to substrates, should coat such substrates uniformly and should adhere to them firmly until removal is desired. Further requirements are that the resist, when exposed to incident radiation, should undergo a substantial change in physical properties, thus to provide a clear distinction between the exposed and unexposed portions so as to facilitate the selective removal of one or the other from the substrate when desired.

As has been indicated, numerous compositions for use in photo-resistive processes have been developed. As has also been explained, these fall generally into the "positive" or "negative" resist categories depending upon whether selective removal or selective retention of the exposed portions of resist is contemplated. Negative photo-resists, in general, operate through a bond formation mechanism, usually a crosslinking or polymerization. Thus such resist formulations generally comprise monomers which polymerize or polymers which crosslink upon exposure to radiation. It may thus be seen that the effective molecular weight of the system is increased in negative resist formulations such that differential removal of those portions not irradiated is facilitated. A frequent means for effecting such removal is solvent dissolution, but other means such as vaporization may also be employed. The positive resists on the other hand operate usually via a bond cleavage mechanism whereby the molecular weight is decreased. Thus the exposed portions of positive resist formulations are differentially removed in such systems.

The materials and processes of this invention are also admirably suited for employment in the photographic art. Those skilled in the art will understand that the beneficial properties of the materials and the advantageous aspects of the properties are also applicable to photographic systems. Thus, photographic materials and systems having excellent sensitivity, resolution and efficiency may be formulated with these materials and processes. In addition, the materials of the invention are known to display a wide spectrum of vivid colors upon polymerization thus leading to novel color photographic materials.

It will be seen that preferred embodiments of the materials and processes of this invention employ monolayer and multilayer structures which comprise pluralities of domains of the materials, which domain have regular structures. Such domain assemblages are thought to lead, in part, to the superior properties displayed herein.

DESCRIPTION OF THE PRIOR ART

The DeForest text, which will be recognized by those skilled in the art as being a preeminent work in the field, provides an instructive background for the understanding of negative photo-resists. Thus, it is known to include cinnamic acid derivatives in photo-resistive compositions to take advantage of the cinnamates' tendency to form intermolecular crosslinks upon irradiation. One such derivative is the cinnamyl ester of polyvinyl alcohol which has been used as a resist since 1953; polystyrene-cinnamate formulations have also been used. It has been reported that cinnamylidene acrylic acid ester has shown a high photo-reactivity in resist compositions. U.S. Pat. No. 3,767,415 issued to Tanaka, teaches the use of polyvinyl cinnamylidene acetate in such systems.

The DeForest reference describes numerous isoprenoid rubber moieties especially "cyclized" isoprenoids which are suitable for use in photolithography, especially on a macro scale. DeForest further explains the almost universal inclusion of photo-sensitizers in commercial negative resist formulations even in those systems employing monomers having substantial photo-reactivity in their own right.

Additional negative resist systems have been reported which are especially useful for electron beam radiant polymerization or crosslinking. Thus, epoxidized polybutadienes, polysiloxanes and polyacrylic species especially poly(glycidyl) methacrylate-co-ethyl acrylate) have been reported as being useful. See the Thompson and Kerwin article cited above.

U.S. Pat. No. 3,840,369 issued to Carlick et al, teaches the use of isocyanate-modified polyfunctional ethylenically unsaturated monomers in photo-resist formulations. The use of thienyl acrylic species in negative resist systems is disclosed by Satomura in U.S. Pat. No. 3,945,831.

The Spiller and Feder article discloses other resistive systems including polymethyl methacrylate, poly(buten-1) sulfone, polyvinyl ferrocene, barium-lead acrylate, polybutadiene, poly-(diallyl orthophthalate), poly(dichloropropyl acrylate) and epoxidized polybutadiene.

The use of diacetylenes in photographic and other arts is disclosed in certain U.S. Patents. Thus, U.S. Pat. Nos. 3,501,297 issued to Cremeans, 3,501,302 issued to Foltz, and 3,501,303 issued to Foltz et al bear a common assignee and share similar disclosures. These patents disclose dispersions of crystals of certain diacetylenes in carrier means for the formulation of direct imaging photo-reactive compositions. As taught by these patents, certain microcrystalline diacetylenes may be rigidly held in a resin, gelatin, or gum matrix, selectively exposed to light, and caused to evidence a color change in the areas which were illuminated. A quantum efficiency of 8 to 16 is reported.

U.S. Pat. No. 3,501,308 issued to Adelman also provides microcrystalline diacetylenes in a binder for photographic purposes. In addition, however, an organic pi-acid electron acceptor is admixed to improve the sensitivity of the compositions. U.S. Pat. No. 3,679,738 issued to Cremeans is drawn to crystalline photosensitive diacetylenes having a particular chemical formula which includes an alkali metal carboxylate. Photosensitive coatings are provided by dispersing the fine crystals in a binder matrix.

U.S. Pat. No. 3,723,121 issued to Hauser relates to thermochromic laser bleaching of pre-formed polymers of diacetylenic species.

U.S. Pat. No. 3,743,505 issued to Bloom et al discloses the use of amine salts of diacetylenic carboxylates in photographic processes. While native crystals of polyacetylenes may be deposited in a substrate from solution, such crystals are preferably dispersed in a carrier means or binder.

Guevera et al in U.S. Pat. No. 3,772,011 provides a diacetylenic composition which undergoes direct image-wise photopolymerization to a highly colored polymeric product when elaborated into a layer of microcrystals contiguous to a photo-conductive layer. Such polymerization takes place upon exposure during the application of an electric potential across the layers. In some cases, an organic photoconductor may be included in the layer of crystalline polyacetylenes.

U.S. Pat. No. 3,772,027 issued to Luckey provides crystalline polyynes with improved sensitivity and with extended absorption spectra through the inclusion of inorganic salt sensitizers. U.S. Pat. No. 3,772,028 issued to Fico et al obtains the same result with the inclusion of pyrylium or thiopyrylium salts. Similar improvements in sensitivity are obtained in such systems by Ehrlich in U.S. Pat. No. 3,811,895. Therein is disclosed the use of organometallics as sensitizers and the use of such sensitized systems as X-ray film media.

"Amplification" of poorly imaged crystalline diacetylenic compositions is obtained by U.S. Pat. No. 3,794,491 issued to Borsenberger et al. Faint images are enhanced through postexposure irradiation.

In an effort to secure diacetylenic imaging compositions having much greater resolution, Rasch in U.S. Pat. No. 3,822,134, prepared compositions having a much finer grain structure than before. Use of vapor deposition in vacuo facilitates the isolation of such fine microcrystals.

U.S. Pat. No. 3,844,791 issued to Bloom et al discloses preferred constituents for dispersed crystal polyacetylenic photosensitive compositions. Thus, ammonium carboxylates are included in diacetylenic moieties to improve the sensitivity thereof. In a related U.S. Pat. No. 4,066,676, Bloom et al provide amine salts for such inclusions.

An article by Khimii found in *Russian Chemical Reviews*, vol. 32, no. 5, pp 229-243 (1963), disclosed on page 242 that certain polyacetylenes display a high photoelectric sensitivity in modulated light.

Bohlmann, writing in *Angewandte Chemie*, vol. 65, no. 15, pp 385-408 (1953), relates the use of certain polyacetylenes as X-ray photographic substrates.

U.S. Pat. No. 3,702,794 issued to Hartlein discloses the improvement in adhesion between siliceous materials and polyolefins such as polypropylene and polyethylene through the use of a silane and chlorinated organic compound.

U.S. Pat. No. 4,154,638 issued to Franz, et al discloses the use of silicon-functional terminal groups in a multifunctional silane primer for use as a coupling agent between organic polymers and inorganic species which have been functionalized with tin or similar metal groups.

U.S. Pat. Nos. 3,911,169 and 4,103,045 both to Lesaicherre, et al disclose processes for improving of adhesion of coatings of photo-resists to surfaces of inorganic oxides. Amino silanes, polysilazanes, and cyclopolysiloxanes are disclosed as promoting the adhesion of polymeric resists to oxide coatings. No disclosure of covalent bonding is made.

None of the compositions, processes, or articles described or referred to above anticipates or renders obvious the subject matter of the instant invention.

SUMMARY OF THE INVENTION

Figure 1:
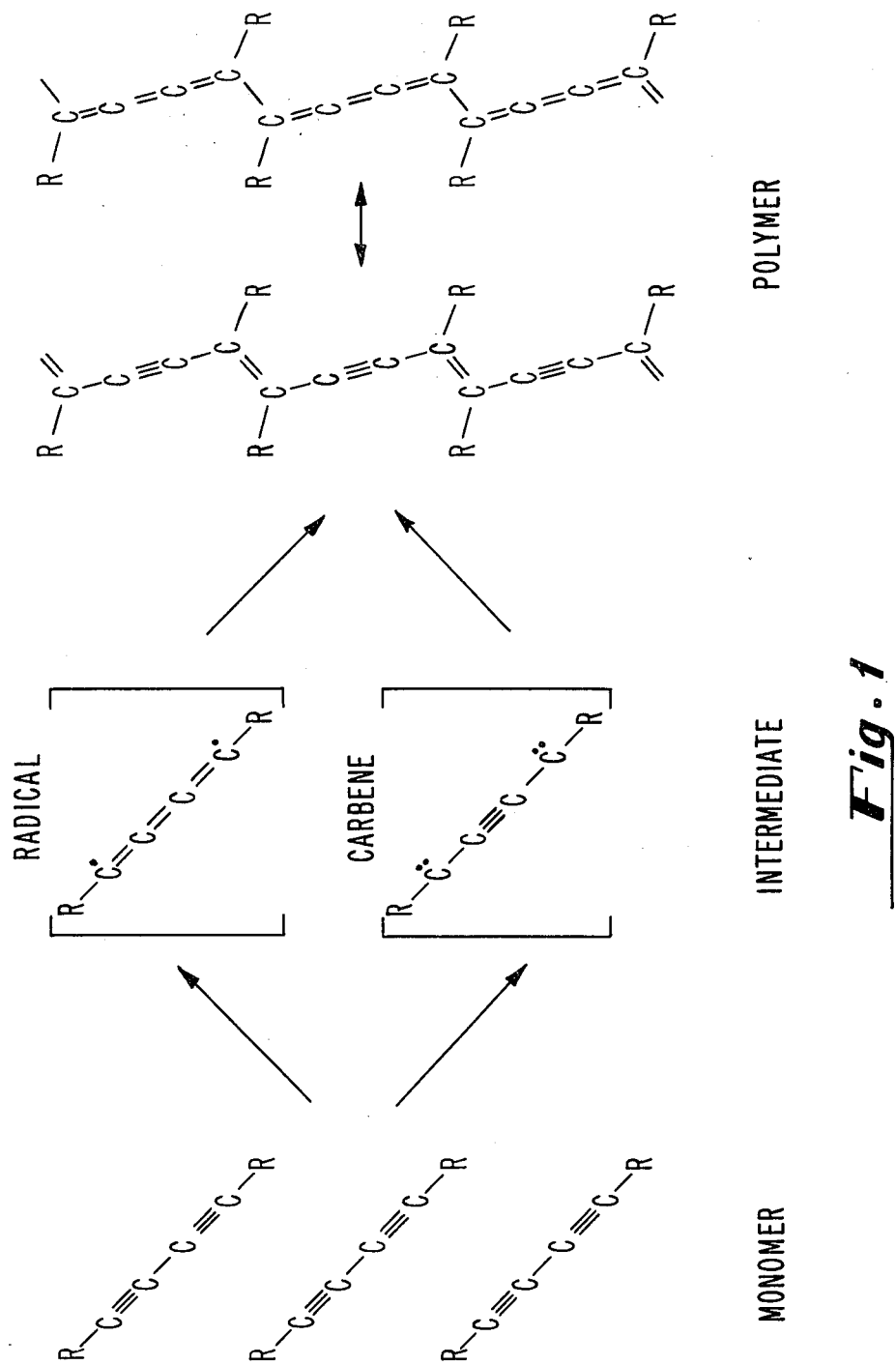
FIG. 1 is a schematic representation of the polymerization of the compositions of the invention according to the processes of the invention, whereby a mechanism is postulated. The regularity of assemblages of monomer and of the resulting polymer is shown.
Figure 2:
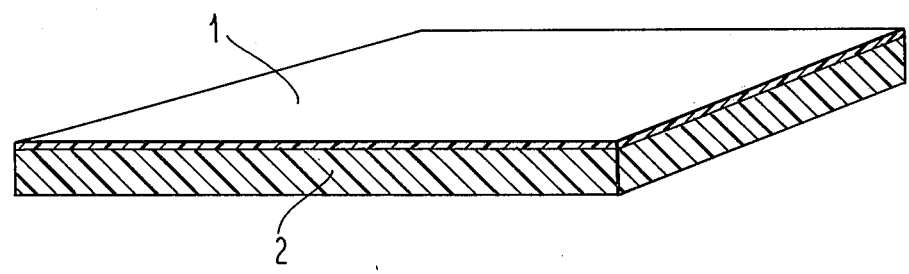
FIG. 2 is a representational view of certain embodiments of the present invention, especially photographic film. Thus 1 represents a coating comprising the materials of the invention; while 2 refers to a substrate which may comprise either one or a plurality of layers. It is to be understood that coating 1 may be a monolayer, multilayer, or other coating. Additionally, substrate 2 may comprise inhomogeneous material or aggregates. In one embodiment, substrate 2 comprises a flexible film while coating 1 is one or more layers, of diacetylenic materials; in another, 2 is doped silica.
Figure 3:
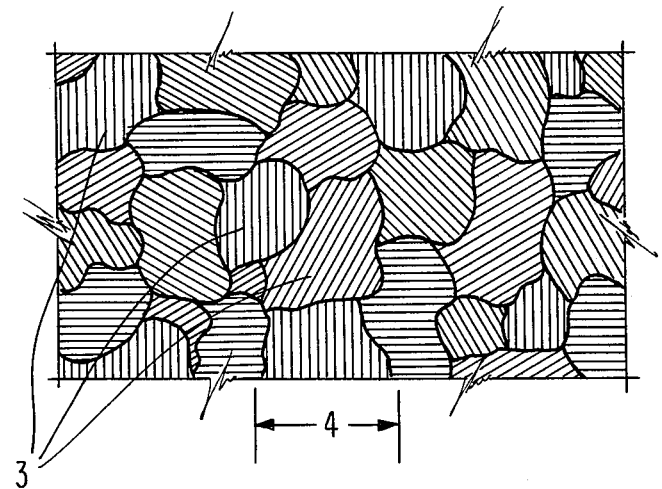
FIG. 3 is intended to suggest the domain micro structure of certain preferred embodiments of the invention. Thus, domains such as those indicated by 3, are present, which domains have substantially regular arrays of constituent molecules. The orientations of these arrays are to be implied from the hatching placed thereupon. Reference No. 4 is intended to suggest the average dimension of a domain according to preferred forms of the invention.

In general, the novel processes of this invention are useful in the formulation, application and use of photographic, photolithographic and photo-resistive compositions. Thus, the processes provide for novel means of photography, macro and micro lithography, printing, etching, and engraving and for the elaboration and fabrication of micro structures, especially those useful in the electronics and integrated electronics fields. In addition, the use of certain genre of chemical compositions in the processes of the invention is taught together with the elaboration and fabrication of articles utilizing the novel compositions and processes taught herein.

The photo-resistive processes of the invention are characterized as demonstrating superior performance in the elaboration and fabrication of electronic microstructures, as requiring lesser amounts of radiant energy in use, and as enabling a significantly more detailed resistive pattern structure to be composed upon the surface of a substrate. Thus, the processes of the invention utilize a genus of photo-resistive material which is energy efficient. This energy efficiency may be demonstrated by comparison of an X-ray photo-resist recording to the present invention with typical members currently in use in the art. The Spiller and Feder article reports that from 1 to about 60 joules per cubic centimeter absorbed dose is required for currently used negative X-ray resists. In contrast, the composition of the invention require only about 0.001–0.01 joules per cubic centimeter for polymerization. This high efficiency is manifested by short exposure times and concomitant savings in radiant energy output, in time, and in production costs.

The materials used are negative in mechanism, that is, upon exposure to radiant energy, they polymerize to form areas of polymer which are differentially retained upon exposure to a solvent as compared to the unexposed areas of photo-resist. The materials are further characterized as having a physical and electronic structure which is uniquely suited to polymerization thus exhibiting an excellent overall efficiency or quantum yield of polymerization upon exposure to radiant energy.

A further aspect of the composition used in the practice of the invention also stems from the unique physical and electronic structure of the composition. The regularity exhibited by the compositions is such that extremely fine exposure patterns may be resolved in the photo-resistive materials formed thereby. For example, X-ray photoresistive compositions currently in use permit resolution of structures on the order of 10,000 Å and to 2000–3000 Å in extreme cases. The compositions of this invention may be employed to permit resolution of structure as small as 100 Å. This improvement in resolution leads to an immediate increase in the number of microstructures which may be fabricated on a given surface area of substrate. This increase permits the reduction in size of articles made thereby and leads to substantial economic advantage.

It is known that amorphous polymer resists undergo physical "relaxation" phenomema in certain systems which lead to microstructural line indistinction and blurring. Additionally, it is known that most systems known to the prior art experience some dissolution of polymer intended to remain during the dissolution and removal step thus leading to edge undercutting. The compositions of the present invention are ideally suited to overcome these problems however. Upon exposure to incident radiation the compositions polymerize into regular polymers with great facility and with high efficiency. The resulting polymers possess physical properties which are vastly different from the unpolymerized compositions. Especially significant is the large difference in solubility between the species; indeed the polymerized compositions are virtually insoluble in commonly employed solvents as compared with the unreacted compositions. As a result, therefore, the unexposed, and consequently unpolymerized, areas are removed almost entirely by exposure to solvent while the exposed regions remain almost totally intact and in place. At the same time, the extreme regularity of the polymerization process and the geometric similarity of the polymers thus formed to their constituent monomers minimizes the "relaxation" experienced by the system upon polymerization. Thus line definition is sharp and blurring avoided.

Additional advantages also obtained through the use of the compositions and processes of this invention. Thus, the compositions of the invention need not employ a sensitizer although one may be employed if desired. Furthermore, the processes of the invention may employ coating techniques which lead to extreme uniformity of substrate coverage and result in similar uniformity of lithographic resolution and clarity.

One embodiment of the present invention includes materials which liberate radical trapping agents upon the application of heat. Such compounds, such as dimers of nitroso compounds which are known in the ethylenic system (see U.S. Pat. No. 4,168,982 issued to Pazos) serve to reduce thermal polymerization and avoid "undercutting". It has been discovered that diacetylenic systems are particularly benefitted by their inclusion.

The compositions employed in the processes of the invention demonstrate superior adhesion to substrates and exhibit a high degree of dissimilarity in physical properties upon polymerization thus leading to ease of processing and superior results. Indeed a preferred form of the invention employs siloxyl moieties to form covalent bonds between the photoresistive layer and the substrate to result in extremely good adhesion between the substrate and the resist. Other forms of covalent bonding may also be employed.

The utilization of the materials and processes of this invention in photographic systems such as, for example, in photographic films is similar in some respects to use as a photoresist. Thus, thin film or collections of films employing the materials of the invention may be employed as either a direct print positive photographic film, or as a negative film. The variety and intensity of colors which are known to be possessed by these materials upon polymerization lend them to color photography, while their extreme resolution and sensitivity result in photographic materials of unparalleled resolving power and efficiency.

Briefly stated, the compositions useful in the practice of the processes of the invention comprise photoresistive materials comprising one or more members of the class of chemical compounds known as diacetylenes. Diacetylenes may be seen to possess at least two carbon-carbon triple bonds (acetylenic bonds) at least two of which triple bonds are in conjugation one with another, i.e., exist in a 1–3 relationship as is illustrated:

$$R_1-C\equiv C-C\equiv C-R_2 \qquad \text{I.}$$

As is known to those skilled in the art, an acetylenic bond possesses a generally linear geometry. It follows that diacetylenes possess a generally linear arrangement of six atoms, the four carbon atoms participating in the diacetylenic "backbone" and each of the two atoms bonded to either end of that backbone. In addition, it is apparent that the diacetylenic structure, being rich with electron density, possesses a novel electronic structure. It is this electronic and geometric structure possessed by the genus of diacetylenes which is believed to contribute in major degree to the unique suitability of such compounds for inclusion in photoresistive and other compositions as taught by this invention.

Diacetylenes which are suitable for use in the practice of this invention conform to the general formula:

$$R_1-C\equiv C-C\equiv C-R_2 \qquad \text{I.}$$

where $R_1$ and $R_2$ may be the same or different and may comprise alkyl, aryl, alkaryl, or aralkyl groups having from one to about 50 carbon atoms. $R_1$ and $R_2$ may, in addition, have heteroatomic substitutions or unsaturations. Thus, $R_1$ or $R_2$ may include one or more ester, acid, alcohol, phenol, amine, amide, halogen, sulfonyl, sulfoxyl, sulfinyl, silyl, siloxyl, phosphoro, phosphato, keto, aldehydo, or other moieties. In addition, metal modifications of any of the foregoing may be included such as, for example, acid or phenolate salt. In addition $R_1$ or $R_2$ or both may be ester, acid, alcohol, phenol, amine, amide, halogen, sulfonyl, sulfoxyl, silyl, siloxyl, phosphoro, phosphato, keto, aldehydo or a metal salt or phenolate. In short, it is contemplated that any diacetylene may be suitable for use in the practice of one or more of the embodiments of the invention with the exception of those diacetylenes wherein $R_1$ or $R_2$ or both are hydrogen. The latter compositions are not suitable due to the fact that they are, in general, explosive.

It is to be understood that the species referred to in this description of the invention may be either straight chain, cyclic, aromatic, or branched. It should also be understood that reference to the composition of this invention as being diacetylenes does not foreclose the presence of additional acetylenic bonds therein. Thus, compositions having 3, 4, or more acetylenic bonds are foreseen as long as at least two or more of such bonds are in conjugation one with another. Furthermore, additional sites of unsaturation may be present such as carbon-carbon, carbon-oxygen, carbon-nitrogen, or other double bonds, aromatic or heteroaromatic species. Substitution with halogens, hydroxyls, amines, thiols, silyls, siloxyls, phosphates, sulfates, sulfonates, or other functionalities is also useful.

For the practice of certain embodiments of the invention, diacetylenes may preferably possess the general formula:

$$R_3-C\equiv C-C\equiv C-R_4 \qquad \text{II.}$$

wherein $R_3$ is a hydrophobic chemical moiety and $R_4$ is a hydrophilic chemical moiety. Those skilled in the art will recognize that "hydrophobic" is a term descriptive of chemical moieties or residues which are, in general, unattracted to water or electrically charged species. Thus, hydrocarbon structures which are unsubstituted or sparingly substituted with heteroatomic funtionalities are considered hydrophobic. In contrast, a "hydrophilic" moiety is one which is attracted to water or electrically charged species and is considered to be one which is substituted with heteroatomic substituents. Thus, hydrophilic species possess one or more acid, ester, alcohol, amino, thiol, or similar heteroatomic substitutents while hydrophobic species are characterized by a substantial lack thereof. Of special utility in the practice of the invention are diacetylenes of formula (II) wherein the substituent $R_3$ comprises a hydrocarbon moiety having from one to about 30 and preferably from 2 to about 20 carbon atoms and wherein $R_4$ may be represented by the formula:

$$-R_5-(A)_n \qquad \text{III.}$$

wherein $R_5$ is a hydrocarbon having from one to about 50 and preferably from one to about 30 carbon atoms; n is an integer from one to about 10 and preferably one to three; and A is a member of the group consisting of halogen, COOH, $COOR_6$, $CONH_2$, $CONHR_6$, OH, SH, $NH_2$, $NHR_6$, $N(R_6)_2$, silyl, siloxyl, sulfate, sulfonate, phosphate and others where $R_6$ is a hydrocarbon having from one to about 8 carbon atoms. Certain preferred forms of the composition include styryl moieties in the hydrocarbon portion of $R_3$ or include other polymerizable unsaturations such as, for example, dienyl, vinyl or acrylic species.

Certain embodiments of the invention may usefully be accomplished utilizing compositions of the formula:

$$R_3-C\equiv C-C\equiv C-R_3 \qquad \text{IV.}$$

or $$R_4-C\equiv C-C\equiv C-R_4 \qquad \text{V.}$$

where $R_3$ and $R_4$ have any of the identities attributed to them above.

Additional embodiments of the invention may profitably employ diacetylenes of formula (I) where $R_1$ or $R_2$ or both have the formula:

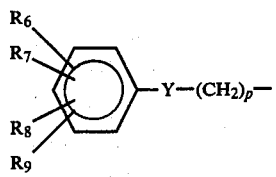   VI.

where p is an integer from 0 to about 20 preferably from one to about 10; Y is O, NH, S, $SO_2$, $SO_3$, $SiO_2$, $PO_3$, $PO_4$, $CH_2$, amido, acetyl, acetoxy, acrylyl, methacrylyl, or styryl,; and $R_6$ through $R_9$ may be the same or different and may be H; $NO_2$; $NH_2$; monohalomethyl; dihalomethyl; trihalomethyl; halogen; alkyl, alkenyl, or aryl having from one to about 6 carbon atoms; $SO_2$; $SO_3$; $PO_3$, $PO_4$, siloxyl; silyl etc. In certain preferred compositions, ethylenic groups are included to result in styryl diacetylenic formulations. In certain compositions, centers of chirality or asymmetry may be present in the molecular structures and optically active materials may be utilized for certain embodiments. Thus, materials may be utilized such as, for example, those of formula (I) wherein $R_1$ or $R_2$ or both have the formula:

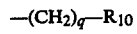   VII where q is an integer from 0 to about 20 and $R_{10}$ is a species having a chiral or optically active center. While it is to be understood that any substitutent having an optical center is contemplated for use herein, several exemplary embodiments may be represented by the formulae:

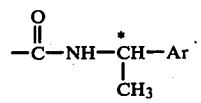   VIII.

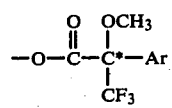   IX.

or,

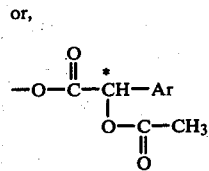   X.

wherein an asterisk indicates an optical center and Ar represents an aromatic group, preferably phenyl or naphthyl. In similar fashion, chiral amino acid or other optically active residues may be included in the diacetylenic compositions of the invention.

In some embodiments of the invention, especially those in which polymerization by UV or X-ray radiation is desired, it has been found convenient to include a number of heteroatomic species in the compositions of the invention. Thus halogens, especially fluorine; sulfur; selenium; phosphorus and similar atoms are preferably included. This is done inter alia to improve the cross section of energy which may be absorbed by the composition, thus to improve its overall efficiency. Of especial note is the employment of polyfluoroalkyl substituents in the practice of the invention for this purpose; specific use of such moieties is contemplated hereby.

It should be apparent from the foregoing that no limitation is intended or is to be implied with respect to the diacetylenes suitable for the practice of one or more embodiments of this invention. All compositions which include one or more chemical species having at least two acetylenic bonds, at least two of which are in conjugation one with another are suitable.

Exemplary syntheses of diacetylenes are presented in "Synthesis of N-(nitrophenyl)amine Substituted Diacetylene Monomers", Garito et al, *Makromolecular Chemie* (in press); "Synthesis of Chiral Diacetylene Polymers", Garito et al, *Makromolecular Chemie* (in press); "The Chemistry of Diacetylenes", Keter Pub. House, Jerusalem (1974); "Synthesis of Nitrophenoxymethyl Subsituted Diacetylene Monomers", Kalyanaraman, Garito, et al, *Makromolecular Chemie*, vol. 180, June 1979; "Solid-State Synthesis and Properties of the Polydiacetylenes", Baughman et al, *Annals of NY Academy of Science*, vol. 313, (1978); "Polymerization of Diacetylene Carbonic Acid Monolayers at the Gas-Water Interface." Day et al, *J. Polymer Sciences, Polymer Letters ed.* vol. 16, p. 205 (1978); and U.S. Pat. No. 3,923,622 issued to Baughman et al.

As a class, diacetylenes exhibit uniquely regular structures in thin films, multi-layer films, and polymers formed therefrom. In thin films formed on substrates, diacetylenes assume a regular orientation. Upon polymerization, this regular orientation is, to a large degree, maintained resulting in polymers having a regular orientation. This phenomenon which is illustrated in FIG. 1 is known. See "Kinetics of Thermal Polymerization in the Solid State: 2,4-Hexadiyne-1,6 Diol Bis(p-Toluene Sulfonate), Garito et al, *J. Polymer Sci.* 16, 335–338 (1978); "Kinetics of Solid State Polymerization of 2,4-Hexadiyne-1,6-Diol-Bis(p-Toluene Sulfonate)", Garito et al, *Molecular Metals*, Hatfield ed. (Plenum, 1979); Wegner "Recent Progress in the Chemistry and Physics of Poly(diacetylenes)", *Molecular Metals*, W. E. Hatfield ed. Plenum (1979). Additional reports are contained in *Journal of Polymer Science, Polymer Chemistry Ed.* vol. 17, pp 1631–1644 (1979). "Polymerization of Diacetylenes in Multi-Layers", by Wegner et al; and *Macromolecular Chemistry*, vol. 179, pp. 1639–1642 (1978) "The Quantum Yield of the Topochemical Photopolymerization of Diacetylenes in Multi-Layers" by Wegner et al. Reference is specifically made to those reviews and to the references cited therein. Garito and Wegner report on the chemistry, synthesis, structure, orientation and polymerization of diacetylenes and poly (diacetylenes) and describe the multi-layer behavior of certain species thereof. The regular orientation in a thin film has been reported to be in a "herringbone" array. The arrays may be quite large and may, it is believed, extend over the entire area of the film. Wegner has observed large domains thought to be formed of areas of regular orientation. It is possible to form single domain films which can polymerize into single domain polymers.

The chemical molecular structure of such polymers, while not entirely clear, is subject to interpretation. As shown in FIG. 1, polymers of diacetylenes are believed to possess triple and double bonds in a 1-3 relationship in the subunits of the polymer. It will be understood by those skilled in the art that the two "resonance structures" indicated for the polymer represents the fact that, with poly (diacetylenes) as with most organic molecules, structural description in terms of bond order, i.e. triple, double, etc. is less than precise. Thus, with the understanding that the polymers possess bond characteristics which are not fully representable as any one single structure, such polymers will be described as having an acetylenic bond in the subunit thereof. The polymers may be alternatively described as having a repeating subunit wherein four carbon atoms are aligned in a generally linear configuration. Thus, the polymers produced according to the practice of this invention may be alternatively described as (1) being substantially regular in orientation, at least within any polymer domain; (2) having an acetylenic bond in the subunit structure thereof, and (3) possessing subunits which have four carbon atoms in a generally linear configuration.

In general, it is possible to coat substrates with diacetylenes and to utilize such coatings for photo-resistive and other purposes. It is believed that the regular orientation of the diacetylenic "backbone" in the layers so formed places the acetylenic bonds in the proper orientation for polymerization to proceed with high efficiency. This factor combined with the amenability of diacetylenes to absorb radiant energy and to undergo photolytic generation of reactive intermediates such as radicals or carbenes causes such oriented arrays of diacetylenes to be highly reactive towards incident radiation and to affect polymerization quickly upon irradiation.

Coating of substrates with diacetylenic compositions is preferably accomplished by the Langmuir-Blodgett technique. This technique, which is well known to those skilled in the art, causes a thin film of diacetylene to be deposited upon the surface of a fluid. The surface layer is then compressed to minimize the surface area occupied by the diacetylene so as to effect a closest packing arrangement thereof. This closely packed and arrayed diacetylenic composition is then transferred to a substrate by dipping. The use of diacetylenes having hydrophobic and hydrophilic substituents on either end thereof facilitates the use of the technique. Multi-layers may be built up sequentially by this technique. These multi-layers may be uniform in composition or may be dissimilar. They may number from two to several hundreds and may, thus, comprise thin or thick films.

Alternative means of placing diacetylenes on substrates may be utilized as well. Thus, the "whirling" technique as described in the DeForest reference, roller coating as is currently practiced in the art, or even dipping may be employed so to apply the diacetylenic species to the substrate. Coating by vapor deposition may also be employed. The thickness of the films employed in the practice of the current invention may vary depending upon the use contemplated therefore. From a few to about 40 Langmuir-Blodgett constructed layers or a comparable thickness of film formed by one of the alternative means is most suited to photoresistive purposes while greater or lesser thicknesses lend themselves to other embodiments such as photography.

The composition useful in the practice of the invention may include species in addition to the aforedescribed diacetylenes. Thus, additional polymerizable materials may be added as may catalysts, photo-initiators, pigments, and fillers. Additionally, organic or inorganic materials may be included to alter the electrical properties of the compositions, especially for use in thin film devices. The additional polymerizable materials which may be included may encompass any of the wide variety of polymerizable species known to those skilled in the art. Olefinics such as vinyl, styryl, arcylic, dienyl, etc. are preferred. Of these, dienyl and acrylic species are preferred. Dimers of nitroso compounds may also be included as indicated above.

The composition may, optionally, contain a sensitizer or catalyst to improve the photochemical interaction between the compositions and incident radiation. Such sensitizers are well known in the art and include, for example, acetophenone, acyloin derivatives, benzophenone, dyes such as indigo derivatives and many other species. The sensitizers may be included in amounts up to about 5% by weight of composition and preferably between about 1% and about 3%. In an alternative embodiment, one or more layers of diacetylenic composition may be "sandwiched" with layers of sensitizer-containing formulation to give good results.

Other compositions may include in the diacetylenic species polymerizable sites in addition to the diacetylenic bonds themselves. Thus, diacetylenic compounds having acrylic, styryl, vinyl or other polymerizable functionalities may be used to good result. In such a case, the polymerization of such additional polymerizable structures may be accomplished concomitantly with or subsequent to the polymerization of the "backbone" diacetylenes. In cases where multiple single layers of oriented diacetylenes are laid down upon a substrate, it may be seen that polymerization of the "backbone" may occur almost exclusively within one layer. The presence of other polymerizable species creates the possibility of inter-layer polymerization or cross linking. The inclusion of styrene residues is especially preferred for this purpose.

For the practice of photography and photolithography it is highly desirable to employ photosensitive materials which combine high resolution with high sensitivity to radiation. Such goal is attained by the present invention through the use of ordered arrays of diacetylenic films of high sensitivity which have arranged in a plurality of domains.

It is believed that the substantially regular array evidenced by the diacetylenic films according to the practice of this invention, especially those elaborated by the Langmuir-Blodgett technique, contribute to high photoreactivity of those films as reflected in the high quantum efficiency alluded to above. While such high efficiency is to be desired from the point of view of speed of reaction and overall savings of energy in use, it will be appreciated that such high efficiency appears to be contrary to the twin goal of high resolution. A photoresist having the high efficiency of the present invention would be expected to evidence uncontrolled polymerization or reaction upon exposure to radiation and to react not only in exposed areas, but also in neighboring, unexposed areas as well. A preferred embodiment of the present invention overcomes this difficulty and provides photoresists having both a very high efficiency and a high resolving power.

This goal may be obtained through a technique whereby substantially ordered or arrayed films on layers of diacetylenes are caused to be arranged in a plurality of domains within the film or layer structure. It will be appreciated that a substantially regular array of molecules will be retained within the domains thus provided, but that the domains will be randomly oriented so that a domain's molecular array orientation will not normally be repeated in the array orientation of its neighbors. Thus, within any domain, a substantially regular array of diacetylenic molecules will prevail, but that array will terminate at the domain boundary. It will be apparent from the foregoing that the sensitivity of the diacetylenic species arrayed within a domain will remain largely unchanged, but that a photolytic reaction initiated in one domain will not normally pass over into neighboring domains. It will similarly be apparent that the above embodiment will yield photographic materials and films of high sensitivity, and resolution.

The arrangement of diacetylenic films into a plurality of domains may be accomplished in a number of ways. Thus a substantially ordered film or layer of diacetylenic material may be heated either conventionally, through laser or microwave heating techniques, or in other ways to accomplish the establishment of the domains. With conventional heating, heating to just below the melting point of the layer is preferred. Alternatively, during the employment of Langmuir-Blodgett film-forming techniques, one may adjust the PH, the temperature, or the specific gravity of the water subphase utilized in the process to cause the assumption of domains in the resulting film. Other techniques will occur to those skilled in the art whereby domains may be established according to the practice of this invention. It will similarly be understood that routine experimentation will be required to establish optimum conditions for domain formation with any given diacetylenic system.

It is believed that the size of the domains produced in the practice of the invention will be reflected in the ultimate resolving power of the photoresist. In practice it has been possible to create domains of average dimension well below 1000 Å but larger and smaller domain sizes are specifically envisioned as well. Thus, preferred embodiment include domains having average dimensions less than about 10,000 Å, and even more preferably less than about 2000 Å.

An alternative procedure to the establishment of domains in the diacetylenic layers is to include molecules of lower polymerizability in the compositions. These molecules may be any of a wide range of materials including certain of the less reactive diacetylenes, long chain olefins or fatty acids. Alternatively, diacetylenic species may be chosen which possess steric or electronic structures which are not entirely favorable to polymerization either by upsetting the substantially ordered array present in the film or layer or by presenting molecules or lesser reactivity to the advancing polymer chain. Such inclusions may be seen to "temper" the reactivity of the films or layers and to provide an alternative means of control of the system.

For certain applications, it is highly beneficial to provide a strong adherence of the coatings to the underlying substrate. It is possible to bond such coatings to substrates covalently utilizing certain techniques. Thus, hydroxyl or other functional groups commonly found on the surfaces of most substrates may be utilized to consummate silyl or siloxyl linkages with a suitably silicon substituted diacetylenic species. See E. P. Plueddemann, "Mechanism of Adhesion Through Silane Coupling Agents" in *Composite Materials,* Brautman, Krock eds. vol. 6, ch. 6, Academy Press (1974). Other means of covalent bonding of film to substrate or of film precursor species to substrate will readily occur to those skilled in the art. Thus, it is desirable to coat the substrate with a composition which may form covalent linkages with such substrate and which may also form covalent linkages with the diacetylenic species which comprise the photoresistive layer. While any composition which will form the covalent bonding may be employed, preferred species for accomplishing such covalent bonding may be represented by the formula:

$$(R_{11}\text{-O})_3\text{-Si}(R_{12})\text{-Z} \qquad \text{XI.}$$

where the $R_{11}$ groups may be the same or different and are hydrocarbyl groups having from 1 to about 6 carbon atoms, where $R_{12}$ is a hydrocarbyl group having from 1 to about 6 carbon atoms, and Z is any substituent which may covalently bond with the diacetylenic specie of choice. Preferably, Z is an amine, and is used to form an amide linkage with a carboxyl group on the diacetylene, but any suitable substituent may be employed. One such exemplary composition is 3-aminopropyltriethoxysilane which is described by formula (XI) when $R_{11}$ is ethyl, $R_{12}$ is propyl and Z is amino. It will be understood that covalent bonds other than the siloxyl and amide bonds described above may be satisfactorily employed in the practice of the invention.

It has also been found that certain nitroso dimers such as 1-nitrosooctadecane dimer, 1-nitrosododecane dimer and 1-nitrosocyclohexane dimer may be included in the photoresistive compositions of the invention to retard thermally-induced polymerization without interfering with the photochemical polymerizations central to use of the materials as photoresists. In this regard, it is believed that the dimer dissociates thermally to species which inhibit polymerization. Thus thermal polymerization is hindered while photochemical polymerization is unaffected. Any other species which reacts thermally to provide radical trapping species is also useful in this regard.

It should be apparent that any form of irradiation may be utilized to effectuate the polymerization of the composition of the invention. Of the forms commonly used, particle beam, electron beam, X-ray, laser and ultraviolet irradiation are most preferred. As should similarly be apparent, irradiation with masking, with a controlled beam or without effective spatial control, that is, whole surface irradiation may be utilized in the practice of one or more embodiments of the invention. In general it is expected that substantial polymerization will occur within irradiated areas of the process of the invention. Substantial polymerization occurs when at least 50% of the monomer species become incorporated in polymer moieties. Preferably 75% and even more preferably 85% or greater incorporation is desired. In the construction of devices which include diacetylenic polymer films as constituents, it may be desirable to polymerize areas uniformly. As has been shown, a selective exposure is desirable for photo lithography and micro-fabrication. Thus either mode of irradiation may be seen to be useful.

For employment as photographic media, it follows that for many uses, response to visible (or infrared) light is frequently desired. Thus the films or other materials may if necessary employ any of the well-known sensitizers to alter the spectral response of the materials and products. Of course, the diacetylenic species which possess inherent sensitivity in the visible (infrared) region are suitable for such use without the use of a sensitizer.

EXAMPLE 1

4-Nitrophenyl propargyl ether:

To a solution of propargyl alcohol (10 g) in DMSO (10 ml) $K_2CO_3$ (1.5 g) was added and the mixture kept stirring. 4-Nitrofluorobenzene (28 g) was added gradually and the mixture stirred at room temperature for three days. It was poured into excess water slightly acidified with HCl. TLC showed two spots, one of which was identical with 4-nitrofluorobenzene. Fractional crystallization from cyclohexane afforded a pale yellow solid (15.8 g, 50%), m.p. 108°–110° C.; I.R. (KBr): 3174(≡CH), 1582, 1315, 847 (Ar-$NO_2$) cm$^{-1}$.

EXAMPLE 2

2,4-Hexadiyn-1,6-diol-bis-(4-nitrophenyl) ether

A solution of the material from Example 1 (1 g) in DMSO (15 ml) was added at 55°–60° C., with stirring, to a mixture of cuprous chloride (1 g) and ammonium chloride (3 g) in water (10 ml), with oxygen passing through the solution. After four hours, the mixture was poured into dilute aqueous ammonium hydroxide solution (500 ml). The yellow ppt. was filtered off, washed with cold water, dried and recrystallized from dioxane-ethanol (1.3 g. 70%), m.p. 213° C. dec.; I.R. (KBr): 1592, 1336, 847 (Ar-$NO_2$)cm$^{-1}$.

EXAMPLE 3

2,4-Hexadiyn-1,6-diol-bis-(2,4-dinitro-5-fluorophenyl) ether

To a solution of 2,4-hexadiyne-1,6-diol (5 g) in DMSO (15 ml), triethylamine (2 ml) was added. To the stirring solution at room temperature, 2,4-dinitro-1,5-difluorobenzene (20 g) was added gradually. After stirring overnight at room temperature, the mixture was poured into water, the product filtered off, washed with water, dried and recrystallized from dioxane-water (16 g., 75%). The compound decomposes about 190° C. without melting. I.R. (KBr): 1587, 1333, 846 (Ar-$NO_2$), 1176 (Ar-F)cm$^{-1}$.

EXAMPLE 4

2,4-Hexadiyn-1,6-diol-bis-(2-nitro-4-trifluoromethylphenyl)ether

Reaction of 2,4-hexadiyne-1,6-diol (1 g) with 4-fluoro-3-nitro-benzotrifluoride (4 g.) following the procedure of Example 3 yielded the desired product. Recrystallization from ethanol gave pale yellow needles. (1.1 g., 25%) m.p. 137° C. I.R. (KBr): 1620($NO_2$), 1120 682 ($CF_3$)cm$^{-1}$.

EXAMPLE 5

4-Nitrophenyl 1-Bromopropargyl ether

To a solution of KOBr in water (from 22 g. KOH, 5 ml. $Br_2$ and 100 ml water) at 0° C., 4-nitrophenyl propargyl ether (3.5 g) in dioxane (80 ml) was added dropwise with stirring. After stirring an additional 15 minutes, the solution was poured into excess ice water and the precipitate was filtered off and recrystallized from dioxane as a white powder (4.5 g., 90%), m.p. 156°–157° C. I.R. (KBr): 1587, 1324, 847 (Ar-$NO_2$)cm$^{-1}$.

EXAMPLE 6

1-(4-Nitropehenoxy)2,4-hexadiyne-6-ol

To a suspension of cuprous chloride (20 mg), ethylamine (70%, 1.4 ml) and hydroxylamine hydrochloride (0.12 g) in water (5 ml), a solution of propargyl alcohol (1 g) in DMSO (2 ml) was added with stirring. To the yellow mixture, the bromo ether of Example 5 (0.6 g.) in DMSO (20 ml) was added dropwise at 20° C. over 40 mins. After stirring for an additional one hour, the solution was poured into excess water, the yellow precipitate filtered off and recrystallized from methanol as short needles (0.4 g., 74%), m.p. 172°–173° C. I.R. (KBr): 3448(—OH), 1582, 1333, 846(Ar-$NO_2$)cm$^{-1}$.

EXAMPLE 7

1-(2,4 dinitrophenoxy),6-(4-nitrophenoxy) 2,4-hexadiyne

The material of Example 6 (0.23 g.) was dissolved in DMSO (3 ml) and triethylamine (0.5 ml) was added to the stirring mixture at room temperature, 2,4-dinitrofluorobenzene (0.2 g.) was added dropwise. After stirring for four hours, the reaction mixture was poured into water, the precipitate filtered off and recrystallized from dioxane to afford pink crystals (0.35 g., 88%), m.p. 125° C. I.R. (KBr): 1589, 1333, 846(Ar-$NO_2$)cm$^{-1}$.

EXAMPLE 8

N-(2-Propynyl)-2-methyl-4-nitroaniline

To a suspension of potassium carbonate (20.0 g) in DMSO (7 ml) was added triethylamine (3 ml) and 2-propyn-1-amine (7.10 g, $1.29 \times 10^{-1}$ mole). 2-Fluoro-5-nitrotoluene (20.00 g, $1.29 \times 10^{-1}$ mole) was added with stirring and the reaction mixture was heated at 50° C. for three days. The mixture was cooled, poured into excess water, and extracted with methylene chloride. The methylene chloride solution was dried over sodium sulfate, filtered and evaporated. The residue was chromotographed on a silica column, eluting with benzene, and recrystallized from benzene to afford yellow crystals; m.p. 121°–123° C. Yield: 15.02 g (61%). I.R. (KBr): 3344 (NH), 3226 (CH), 1580 and 1282 cm$^{-1}$ (Ar-$NO_2$).

EXAMPLE 9

N,N'-Bis(2-Methyl-4-nitrophenyl)-2,4-hexadiyn-1,6-diamine

To a suspension of $Cu(OAc)_2.H_2O$ (1.5 g) in pyridinemethanol (1:1, 15 ml) was added N-(2-propynyl)-2-methyl-4-nitroaniline (1.00 g, $5.26 \times 10^{-3}$ mole). The reaction mixture was stirred at 50° C. for two hours. The mixture was poured into excess water and filtered. The crude solid was recrystallized from nitromethane to afford yellow crystals. Yield: 0.70 g (71%). The material did not melt below 200° C. but turned red at 150° C. I.R. (KBr): 3390 (NH), 1585 and 1280 cm$^{-1}$ (Ar-$NO_2$).

EXAMPLE 10

N-(2-Propynyl)-4-nitro-2-trifluoromethylaniline

To a suspension of potassium carbonate (20.0 g) in DMSO (7 ml) was added triethylamine (3 ml) and 2-propyn-1-amine(7.92 g, $1.44 \times 10^{-1}$ mole). The reaction mixture was cooled in an ice bath while 1-fluoro-4-nitro-2-trifluoromethylbenzene (30.13 g, $1.44 \times 10^{-1}$ mole) was added gradually with stirring. The mixture was gradually allowed to warm to room temperature and stirred for 24 hours. The reaction mixture was poured into excess water and extracted with ethyl acetate. The ethyl acetate solution was dried over sodium sulfate, filtered and evaporated. The residue was chromatographed on a silica column, eluting with benzene, and recrystallized from benzene to afford yellow crystals; m.p. 71°–72° C. Yield: 24.24 g (69%). I.R. (KBr): 3450 (NH), 3290 (CH), 1588 (Ar-NO$_2$) and 1300 cm$^{-1}$ (CF$_3$).

EXAMPLE 11

N,N'-Bis(4-nitro-2-trifluoromethylphenyl)-2,4-hexadiyn-1,6-diamine

To a suspension of Cu(OAc)$_2$.H$_2$O (4.5 g) in pyridinemethanol (1:1, 30 ml) was added N-(2-propynyl)-4-nitro-2-trifluoromethylaniline (3.01 g, 1.23×10$^{-1}$ mole). The reaction mixture was stirred at 50° C. for two hours. The mixture was poured into excess water and filtered. The crude solid was recrystallized from nitromethane to afford pale pink crystals. Yield: 2.54 g (84%). The material does not melt below 200° C. but turns dark red at 135° C. I.R. (KBr): 3405 (NH), 1580 (Ar-NO$_2$) and 1290 cm$^{-1}$ (CF$_3$).

EXAMPLE 12

N-(2-Propynyl)-2,4-dinitro-5-fluoroaniline

To a suspension of potassium carbonate (6.0 g) in acetone (25 ml) was added triethylamine (1.5 ml) and 2-propyn-1-amine (2.35 g, 4.25×10$^{-2}$ mole). 1,5-Difluoro-2,4-dinitrobenzene (10.00 g, 4.90×10$^{-2}$ mole) was added and the reaction mixture was stirred at room temperature for 24 hours. The mixture was poured into excess water and filtered. The resulting dark solid was chromatographed on a silica column, eluting with benzene, and recrystallized from benzene to afford yellow crystals; m.p. 113°–115° C. Yield: 8.33 g (82%). I.R. (KBr): 3340 (NH), 3280 (CH), 1615, 1260 (Ar-NO$_2$) and 1210 cm$^{-1}$ (Ar-F).

EXAMPLE 13

N,N'-Bis(2,4-Dinitro-5-fluorophenyl)-2,4-hexadiyn-1,6-diamine

To a suspension of Cu(OAc)$_2$.H$_2$O (1.5 g) in pyridinemethanol (1:1, 10 ml) was added N-(2-propynyl)-2,4-dinitro-5-fluoroaniline (1.00 g, 4.18×10$^{-3}$ mole). The reaction mixture was stirred at room temperature for 17 hours. The mixture was poured into excess water and filtered. The crude solid was chromatographed on a silica column, eluting with chloroform ethyl acetate. Soxhlet recrystallization of the resulting solid from ethyl acetate afforded yellow crystals, m.p. 225° C. dec. Yield: 0.21 g (12%). I.R. (KBr): 3360 (NH), 1680 and 1315 cm$^{-1}$ (Ar-NO$_2$).

EXAMPLE 14

Preparation of N-d(+) (α-methylbenzyl)-10,12-Pentacosadiynamide

To a solution of 510 mg (1.36 mmol) of 10,12-pentacosadiynoic acid in 10 ml tetrahydrofuran was added 138 mg (1.36 mmol) of triethylamine. The resulting cloudy solution was cooled to 0° C. and 129 mg (1.36 mmol) of methyl chloroformate was added dropwise over 1 min. A white solid formed immediately upon addition. The mixture was stirred 1 hour at 0° C., then 165 mg (1.36 mmol) of d(+)-α-methylbenzylamine was added and the mixture was heated at reflux for one hour. Gas evolution was evident within five minutes of addition, and ceased after 15 minutes. The mixture was cooled to room temperature and filtered. The filtrate was washed with 10 ml portions of 1 M HCl, water, and saturated aqueous potassium bicarbonate solution, and dried (MgSO$_4$). Evaporation yielded 540 mg (83% crude yield) of a white solid. Recrystallization from ether-petroleum ether gave white crystals, m.p. 65.5°–66.5° C. I.R. film: 1470, 1545, 1640, 2860, 2925, and 3310 cm$^{-1}$. $[\alpha]_D^{31}$(CHCl$_3$)=44°.

EXAMPLE 15

Preparation of N,N'-bis-(α-methylbenzyl)-10,12-docosadiyndiamide

To a solution of 725 mg (2.00 mmol) of 10,12- docosadiyndioic acid in 50 ml THF was added 405 mg (4.00 mmol) of triethylamine. The solution was cooled to 0° C. and 378 mg (4.00 mmol) of methylchloroformate was added dropwise over one minute. The resulting white mixture was stirred one hour at 0° C., the 485 mg (4.00 mmol) of d(+, -α-methylbenzylamine was added. The reaction mixture was heated at reflux for one hour (gas evolution began immediately upon amine addition and ceased after 20 minutes). The mixture was cooled to room temperature and filtered. The filtrate was washed with 25 ml portions of 1 M HCl, water, and saturated aqueous sodium bicarbonate solution and dried (MgSO$_4$). Evaporation yielded 842 mg (74% crude yield) of a white solid, which polymerized rapidly upon exposure to UV light. Recrystallization from ether-petroleum ether gave 456 mg of white crystals, m.p. 87.5°–89° C. I.R. (film): 1530, 1635, 2850, 2920, and 3300 cm$^{-1}$.

EXAMPLE 16

2,4-Hexadiyn-1,6-diol-bis-(2,4-dinitrophenyl) ether

To a solution of 2,4-hexadiyn-1,6-diol (1.1 g) in acetone (15 ml), K$_2$CO$_3$ (0.5 g) was added. To the stirred solution at room temperature, 2,4-dinitrofluorobenzene (3.8 g) was added gradually and the dark red solution stirred overnight at room temperature. It was poured into excess water, the pale yellow solid filtered off, washed with water and dried. Recrystallization from dioxane ethanol gave short, light pink needles, m.p. 210° C. (4.2 g, 95%). I.R. (KBr): 1592, 1333, 834 (Ar-NO$_2$)cm$^{-1}$.

EXAMPLE 17

N-(2-Propynyl)-2,4-dinitroaniline

To a suspension of potassium carbonate (1.0 g) in acetone (10 ml) was added 2-propyn-1-amine (0.26 g, 4.73×10$^{-3}$ mole). 2,4-Dinitrofluorobenzene (1.32 g, 7.10×10$^{-3}$ mole) was gradually added with stirring and the reaction mixture was refluxed two hours. After cooling it was poured into excess water and filtered. Recrystallization of the crude solid from ethanol afforded yellow needles; m.p. 151°–152° C. Yield: 0.99 g (95%). I.R. (KBr): 3367 (NH), 3268 (CH), 1618, 1590, 1333 and 1311 cm$^{-1}$ (Ar-NO$_2$).

EXAMPLE 18

N,N'-Bis(2,4-Dinitrophenyl)-2,4-hexadiyn-1,6-diamine

To a suspension of Cu(OAc)$_2$.H$_2$O (1.5 g) in pyridinemethanol (1:1, 10 ml) was added N-(2-propynyl)-2,4-dinitroaniline (1.00 g, 4.52×10$^{-3}$ mole). The reaction mixture was stirred at 50° C. for 30 minutes. The mixture was poured into excess water, and filtered. The crude solid was recrystallized from nitromethane to afford pale green crystals. Yield: 0.86 g (86%). The compound failed to melt below 200° C. but changed from green to bronze color at 120° C. It could be recrystallized from dioxane to give a different crystal form, appearing as orange crystals which turn deep orange at 140° C. I.R. (KBr): 3380 (NH), 1617, 1592, 1333 and 1312 cm$^{-1}$ (Ar-NO$_2$).

EXAMPLE 19

Synthesis of Diacetylene alkyl-acid monomers

Diacetylene alkyl-acid monomers for use in mono- and multilayer preparations were synthesized by the Chodkiewicz coupling procedure using bromoacetylenes prepared following Strauss. See Chodkiewicz, W. Ann. Chem. (Paris) 2, 853 (1957) and Strauss, et al, Ber. 63B, 1868 (1930). For example, 1-bromo-undecyn-10-oic acid was coupled to tetradecyne to form pentacosa-10,12-diynoic acid. Fifty m.moles of tetradecyne dissolved in 5 ml ethanol was added with stirring to a 50 ml ethanol solution of 100 m.moles ethylamine forming a yellow solution. The stirred solution was cooled to 15° C. and 50 m.moles of 1-bromo-undecyn-10-oic acid dissolved in 60 ml ethanol was added dropwise over 30 minutes while the temperature was maintained at 15°-20° C. After the addition was complete, the reaction mixture was stirred for 3 hours at 15°-20° C. The mixture was then acidified to pH 1 and extracted twice with 100 ml ethyl acetate. The organic layer was separated, dried over magnesium sulfate, filtered through fluorosil and evaporated to give a colorless, viscous oil. The oil was taken up in methanol-petroleum ether and the solution was filtered. Upon cooling of the filtrate, pentacosa-10,12-diynoic acid crystallized as colorless platelets. (m.p. 59°-60° C.). The platelets become an intense blue upon standing in laboratory light for a short time.

EXAMPLE 20

The apparatus used for multilayer preparation consists of a Langmuir trough made of Teflon with dimensions of 12.2×30 cm [area and 2 cm deep]. The surface pressure is applied by a movable Teflon barrier connected to a motor driven screw gear. A Wilhelmy balance is used continuously to measure the surface pressure. The solid substrate is connected to a vibration-free solid rod and moved in and out of the trough using a reversibly geared motor at speeds of 1-3 cm/hr.

A $4\times10^{-3}$ M solution of pentacosa-10,12-diynoic acid in n-hexane was spread on a $1\times10^{-3}$ M solution of cadmium chloride in water. The pH of the CdCl$_2$ solution was previously adjusted to 6.1 using sodium bicarbonate. Successive layers were deposited on the solid substrates at a constant surface pressure of 15 dyne per cm with a dipping speed of 0.5 mm/sec. Surface pressure area curves show that near 23° C. and a surface pressure of about 15 dyne/cm, a monomer molecule occupies 20 Å$^2$. Y type deposition of the layers was observed.

EXAMPLE 21

The amide produced in Example 14 was elaborated into a fourteen, Y-layer, multilayer assembly by the Langmuir-Blodgett technique on a ferric stearate-coated quartz plate and warmed in an oven at 60° C. for two hours followed by slow cooling. The assembly was exposed to either UV or X-ray radiation through a mask giving excellent pattern delineation.

EXAMPLE 22

In separate experiments, 12-30 layers of pentacosa-10,12-diynoic acid were deposited on solid substrate plates such as glass, silicon, and evaporated gold films on glass. Spatially defined regions of the multilayers were polymerized by X-ray exposure through a mask to produce negative resist device patterns on the substrate plates. For example, a 30 multilayer assembly of pentacosa-10,12-diynoic acid on a silicon single crystal substrate plate was positioned behind a metal mask to allow exposure of the multilayer assembly to X-rays through a 5$\mu$ wide by 1 cm long mask line. The total X-ray energy absorbed for polymerization and reresultant pattern delineation was approximately 10 millijoules/cm$^3$. After exposure, the remaining monomer in the unexposed masked regions was dissolved away by rinsing in an organic solvent such as acetone leaving a well-defined line pattern composed of the pentacose-10,12-diynoic polymer on the silicon substrate. After substrate etching (processing) the polymer was removed by washing in a dilute aqueous HF solution.

EXAMPLE 23

Preparation of a Covalently Bound Diacetylene on a Silicon Surface

Silicon plates with an oxide layer 0.65$\mu$ thick were immersed in concentrated nitric acid for 2 hours. After rinsing with water, the water contact angle ($\alpha_w$) was determined to be 44°. After thorough drying, the plates were treated with vapors of 3-aminopropyltriethoxysilane. The substrate was placed above a boiling solution of 2 ml of the silane in 100 ml dry p-xylene under nitrogen for 16 hours. The substrate was bathed in the vapor, the vapor condensing 5 cm above the substrate. The substrate was rinsed in absolute ethanol and water; $\alpha_w$ was determined to be 45°. The silanated substrate was immersed in a solution of 22 mg (0.06 m.mol) of 10,12-petacosadiynoic acid in 10 ml anhydrous pyridine. A solution of 14 mg (0.07 m.mol) of N,N-dicyclohexylcarbodiimide in 1 ml pyridine was added. The wafers were treated for 22 hours at room temperature under nitrogen. The substrate was rinsed with pyridine, ethanol, boiling pyridine, and boiling ethanol and dried. The $\alpha_w$ was determined to be 78°.

EXAMPLE 24

A multilayer assembly of 15 layers of the composition of Example 19 elaborated upon a quartz plate by the Langmuir-Blodgett technique was placed in an oven at 55° C. for 6 hours and then cooled to room temperature. Pluralities of domains were thus established in the assembly which was found to yield excellent definition and reponse upon selective exposure to UV or X-ray radiation.

EXAMPLE 25

Ordinary transparent, flexible film was coated with 15 Langmuir-Blodgett layers of the amide of Example 14. The coated film was heated at 55°-60° C. for 2 hours followed by cooling. The film was then exposed to a test pattern through a lens to afford excellent definition and resolution having a brilliant purple-bronze coloration.

What is claimed is:

1. A photographic or photolithographic article comprising a substrate and at least one substantially continuous layer on said substrate of a polymerizable composition comprising at least one material having at least two acetylenic bonds, at least two of said bonds being in conjugation with one another, said layer comprising a plurality of domains, each of said domains having average dimensions less than 10,000 Angstroms and having a substantially regular array of said composition, so that said layer is imagewise polymerizable with improved resolving power upon the application of radiation to selected portions thereof.

2. The article of claim 1 wherein said layer has been formed by the Langmuir-Blodgett technique.

3. The article of claim 1 further comprising a plurality of said layers.

4. The article of claim 1 wherein said layer is bonded to said substrate by covalent linkages.

5. The article of claim 4 wherein said linkages are siloxyl linkages.

6. The article of claim 1 wherein said material has the formula:

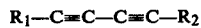

wherein $R_1$ is a hydrophobic chemical moiety and $R_2$ is a hydrophilic chemical moiety.

7. The article of claim 1 wherein said material has the formula:

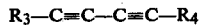

where $R_3$ comprises a hydrocarbyl moiety having from 1 to about 30 carbon atoms and $R_4$ is represented by the formula:

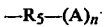

where $R_5$ is a hydrocarbyl group having from 1 to about 30 carbon atoms, n is an integer from 1 to about 6 and A is selected from the group consisting of COOH, $COOR_6$, $CONH_2$, $CONHR_6$, $CON(R_6)_2$, OH, SH, $NH_2$, $NHR_6$, $N(R_6)_2$, silyl, sulfate, sulfinate, phosphate, and siloxyl where $R_6$ is a hydrocarbyl having from 1 to about 10 carbon atoms.

8. The article of claim 1 wherein said material is opticaly active.

9. The article of claim 1 wherein said material has three acetylenic bonds, said bonds being in conjugation with one another.

10. The article of claim 1 wherein said layer further comprises a second polymerizable composition.

11. The article of claim 1 wherein said composition further comprises an amount sufficient to reduce thermal polymerization of a dimer of a nitroso compound.

12. The article of claim 1 wherein said material has been substantially fluorinated.

13. The article of claim 1 wherein said substrate is suitable for photolithographic processing.

14. The article of claim 1 wherein said substrate comprises silicon or silicon dioxide.

15. The article of claim 1 wherein said substrate comprises a lithographic plate.

16. The article of claim 1 wheren said domains have average dimensions less than about 2,000 Å.

* * * * *

UNITED STATES PATENT AND TRADEMARK OFFICE
CERTIFICATE OF CORRECTION

PATENT NO. : 4,439,514

DATED : March 27, 1984

INVENTOR(S) : Anthony J. Garito

It is certified that error appears in the above-identified patent and that said Letters Patent is hereby corrected as shown below:

Col. 9, line 6, "moietiesto" should be --moieties to --.

Col. 14, line 43, after "have" insert --been--.

Col. 24, line 15, correct the spelling of "opticaly" to

--optically--.

Signed and Sealed this

Twenty-eighth Day of August 1984

[SEAL]

Attest:

GERALD J. MOSSINGHOFF

Attesting Officer  Commissioner of Patents and Trademarks